US006419921B1

(12) United States Patent
Négrier et al.

(10) Patent No.: US 6,419,921 B1
(45) Date of Patent: Jul. 16, 2002

(54) DNA-CONSTRUCTS OF BLOOD CLOTTING FACTORS AND P-SELECTIN

(75) Inventors: Claude Négrier, Irigny; Jean Luc Plantier, Lyons, both of (FR)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/440,509

(22) Filed: Nov. 15, 1999

(30) Foreign Application Priority Data

Dec. 2, 1998 (EP) .............................................. 98122883

(51) Int. Cl.[7] ........................ C12N 15/00; A61K 35/14; A61K 39/00; C07H 21/04; A01N 63/00
(52) U.S. Cl. ............................... 424/93.21; 424/192.1; 435/320.1; 435/455; 530/381; 530/384; 536/23.4; 536/23.5
(58) Field of Search .......................... 424/93.21, 192.1; 435/69.1, 320.1, 252.3, 440, 455; 514/44; 536/23.4, 23.5; 530/381, 384

(56) References Cited

U.S. PATENT DOCUMENTS

| 5,198,424 A | 3/1993 | McEver ........................ 514/13 |
| 5,877,289 A | * 3/1999 | Thorpe et al. ............... 530/387 |

FOREIGN PATENT DOCUMENTS

| DE | 98122883.6 | 12/1998 |
| WO | WO 97/11684 | 4/1997 |
| WO | WO 98/42850 | 10/1998 |

OTHER PUBLICATIONS

Ledley et al. Pharmaceutical Research. 13: 1595–1614, Nov. 1996.*
Miller et al. FASEB J. 9: 190–199, Feb. 1995.*
Verma et al. Nature. 389: 239–242, Sep. 1997.*
Blagoveshchenskaya, Anastasia D. et al., "Lysosomal Targeting of P–Selectin Is Mediated By A Novel Sequence Within Its Cytoplasmic Tail", The Journal of Biological Chemistry, vol. 273, No. 5, Jan. 30, 1998, pp. 2729–2737.
Disdier, Magali et al., "Cytoplasmic Domain of P–Selectin (CD62) Contains the Signal for Sorting Into The Regulated Secretory Pathway", Molecular Biology of the Cell, vol. 3, Mar. 1992, pp. 309–321.
Fleming, Judith C. et al., "The Transmembrane Domain Enhances Granular Targeting of P–Selectin", European Journal of Cell Biology 75, Apr. 1998, pp. 331–343.
Green, Samuel A., "The Cytoplasmic Domain of P–Selectin Contians a Sorting Determinant That Mediates Rapid Degradation in Lysosomes," The Journal of Cell Biology, Vol, 124, No. 4, Feb. 1994, pp. 435–448.
Koedam, Joost A. et al., "P–Selectin, A Granule Membrane Protein of Platelets and Endothelial Cells, Follows The Regulated Secretory Pathway in AtT–20 Cells," The Journal of Cell Biology, vol. 116, No. 3, Feb. 1992, pp. 617–625.
Norcott, John P. et al., "Target of P–Selectin to Two Regulated Secretory Organelles in PC12 Cells," The Journal of Cell Biology, vol. 134, No. 5, Sep. 1996, pp. 1229–1240.
Kozak, Marilyn, "Point Mutations Define a Sequence Flanking the AUG Initiator Codon That Modulates Translation by Eukaryotic Ribosomes," Univ. of Pittsburgh, Dept. of Biological Sciences, vol. 44, Jan. 31, 1986, pp. 283–292.
Kurachi, Sumiko et al., "Role of Intron I in Expression of the Human Factor IX Gene," The Journal of Biological Chemistry, vol. 270, No. 10, Mar. 10, 1995, pp. 5276–5281.
Kurachi, Sumiko et al., "Role of Intron I in Expression of the Human Factor IX Gene", The Journalof Biological Chemistry, vol. 270, No. 10, pp. 5276–5281 (Mar. 10, 1995).
Green, Samuel A. et al., "The Cytoplasmic Domain of P–Selectin Contains a Sorting Determinant That Mediates Rapid Degradation in Lysosomes", The Journal of Cell Biology, vol. 124, No. 4, pp. 435–448 (Jan. 1, 1994).
Disdier, Magali et al., "Cytoplasmic Domain of P–Selectin (CD62) Contains the Signal for Sorting into the Regulated Secretory Pathway", Molecular Biology of the Cell, vol. 3, pp. 309–321(Mar. 1, 1992).
Norcott, John P. et al., "Targeting of P–Selectin to Two Regulated Secretory Organelles in PC12 Cells", The Journal of Cell Biology, vol. 134, No. 5, pp. 1229–1240(Sep. 1996).
Plantier, Jean–Luc et al., "P–Selectin Tail Induces The Storage of Factor IX in Cho Cells", Blood, vol. 92, No. 10, pp. 380B (Nov. 15 1998), Abstract.
European Search Report (Apr. 5, 2000).

* cited by examiner

*Primary Examiner*—Deborah J. R. Clark
*Assistant Examiner*—Shin-Lin Chen
(74) *Attorney, Agent, or Firm*—Finnegan, Henderson, Farabow, Garrett & Dunner, L.L.P.

(57) ABSTRACT

A DNA construct is disclosed which encodes a fusion protein comprising an amino acid sequence of a blood clotting factor like Factor IX and an amino acid sequence of the cytoplasmic domain of P-Selectin. Such construct may be used for the somatic gene therapy of patients suffering from a defiency of a blood coagulation factor.

9 Claims, 7 Drawing Sheets

SEQUENCE LISTING

<160> NUMBER OF SEQ ID NOS: 15

<210> SEQ ID NO 1
<211> LENGTH: 35
<212> TYPE: PRT
<213> ORGANISM: Homo sapiens

<400> SEQUENCE: 1

Arg Lys Arg Phe Arg Gln Lys Asp Asp Gly Lys Cys Pro Leu Asn Pro
1               5                   10                  15

His Ser His Leu Gly Thr Tyr Gly Val Phe Thr Asn Ala Ala Phe Asp
            20                  25                  30

Pro Ser Pro
        35

<210> SEQ ID NO 2
<211> LENGTH: 31
<212> TYPE: DNA
<213> ORGANISM: Homo sapiens

<400> SEQUENCE: 2
acacccatgg agcgcgtgaa catgatcatg g                             31

<210> SEQ ID NO 3
<211> LENGTH: 32
<212> TYPE: DNA
<213> ORGANISM: Homo sapiens

<400> SEQUENCE: 3
tggatccatg cagcgcgtga acatgatcat gg                            32

<210> SEQ ID NO 4
<211> LENGTH: 32
<212> TYPE: DNA
<213> ORGANISM: Homo sapiens

<400> SEQUENCE: 4
aaaactcgag ttaagtgagc tttgttttttt cc                           32

<210> SEQ ID NO 5
<211> LENGTH: 33
<212> TYPE: DNA
<213> ORGANISM: Homo sapiens

<400> SEQUENCE: 5
aaaaacgcgt agtgagcttt gttttttcct taa                           33

<210> SEQ ID NO 6
<211> LENGTH: 18
<212> TYPE: DNA
<213> ORGANISM: Homo sapiens

<400> SEQUENCE: 6
aacaacccga tggaagtc                                            18

<210> SEQ ID NO 7
<211> LENGTH: 23
<212> TYPE: DNA
<213> ORGANISM: Homo sapiens

<400> SEQUENCE: 7

-continued aatgacttca ctcgggttgt tgg                                         23

<210> SEQ ID NO 8
<211> LENGTH: 32
<212> TYPE: DNA
<213> ORGANISM: Homo sapiens

<400> SEQUENCE: 8
aaaaacgcgt agaaagcgtt tcagacaaaa ag                               32

<210> SEQ ID NO 9
<211> LENGTH: 31
<212> TYPE: DNA
<213> ORGANISM: Homo sapiens

<400> SEQUENCE: 9
aaaactcgag ttaaggactc gggtcaaatg c                                31

<210> SEQ ID NO 10
<211> LENGTH: 25
<212> TYPE: DNA
<213> ORGANISM: Homo sapiens

<400> SEQUENCE: 10
atttcacagc tgacatcatg tctgg                                       25

<210> SEQ ID NO 11
<211> LENGTH: 23
<212> TYPE: DNA
<213> ORGANISM: Homo sapiens

<400> SEQUENCE: 11
accagctgca atgaaaataa ggg                                         23

<210> SEQ ID NO 12
<211> LENGTH: 26
<212> TYPE: DNA
<213> ORGANISM: Homo sapiens

<400> SEQUENCE: 12
attttgttgg cgttttcatg atcaag                                      26

<210> SEQ ID NO 13
<211> LENGTH: 50
<212> TYPE: DNA
<213> ORGANISM: Homo sapiens

<400> SEQUENCE: 13
aacgcgtatt cttttacatt tcaggtctat ggattctggg gtgccacaac            50

<210> SEQ ID NO 14
<211> LENGTH: 25
<212> TYPE: DNA
<213> ORGANISM: Homo sapiens

<400> SEQUENCE: 14
actcgagtca caacttgaaa ccttc                                       25

<210> SEQ ID NO 15
<211> LENGTH: 33
<212> TYPE: PRT
<213> ORGANISM: Homo sapiens

<400> SEQUENCE: 15

-continued

```
Thr Arg Ile Leu Leu His Pro Arg Ser Met Asp Ser Gly Val Pro Asn
  1               5                  10                 15

Leu Arg Leu Ser Glu Asn Arg His Asp Arg Leu Thr Glu Ser Pro Lys
             20                  25                  30

Ile
```

DNA-CONSTRUCTS OF BLOOD CLOTTING FACTORS AND P-SELECTIN

Figure 1:
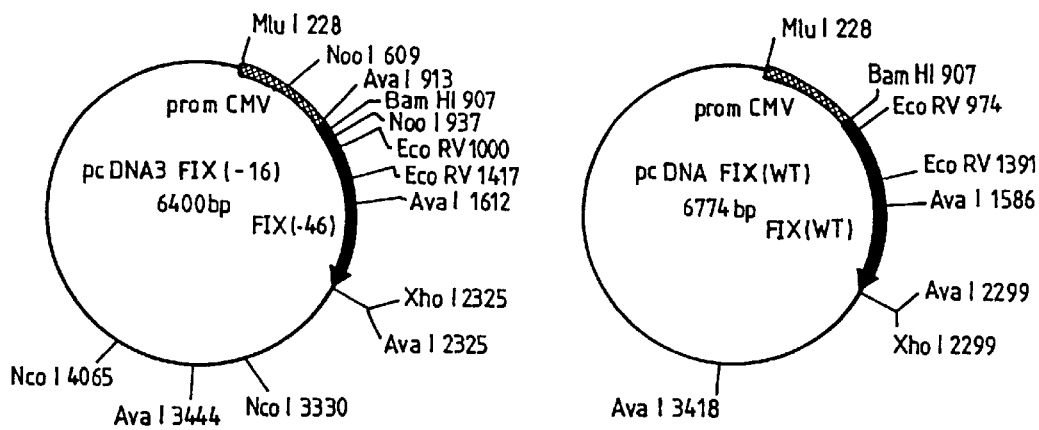
Figure 2:
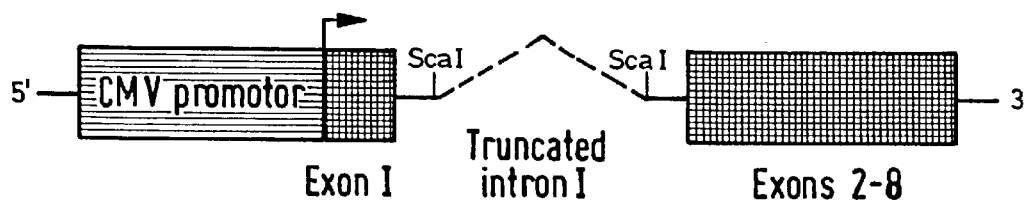
Figure 3:
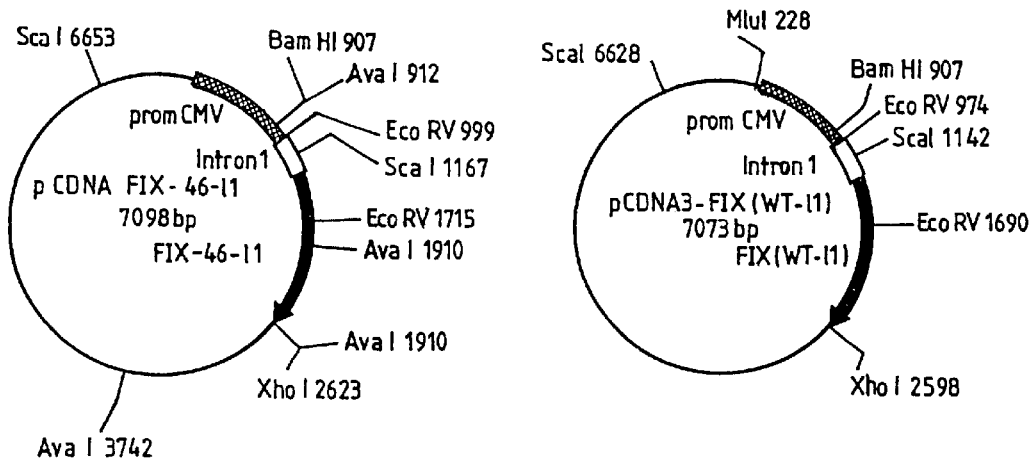
Figure 4:
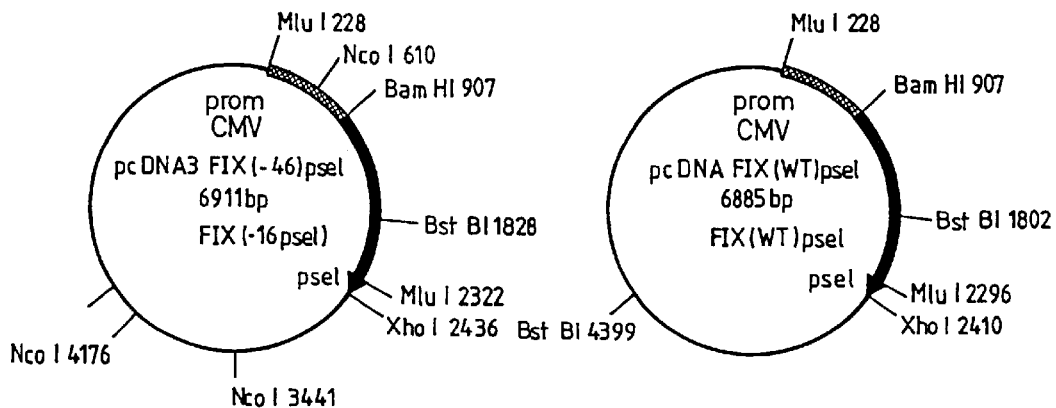
Figure 5:
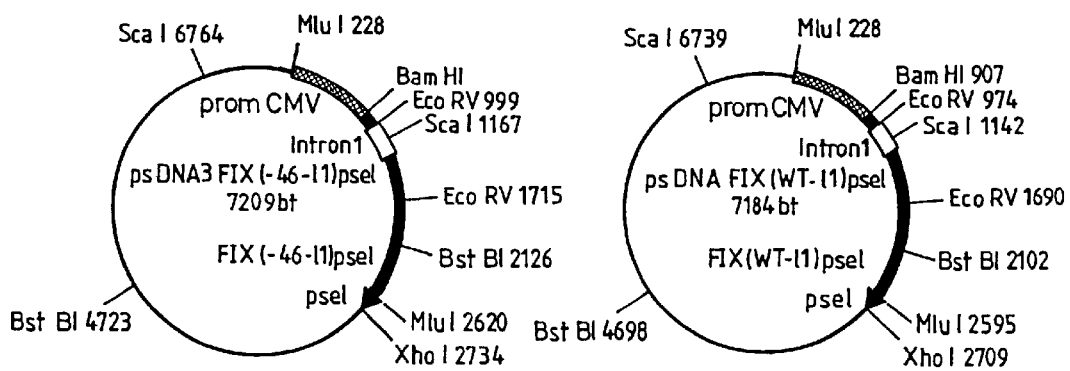
Figure 6:
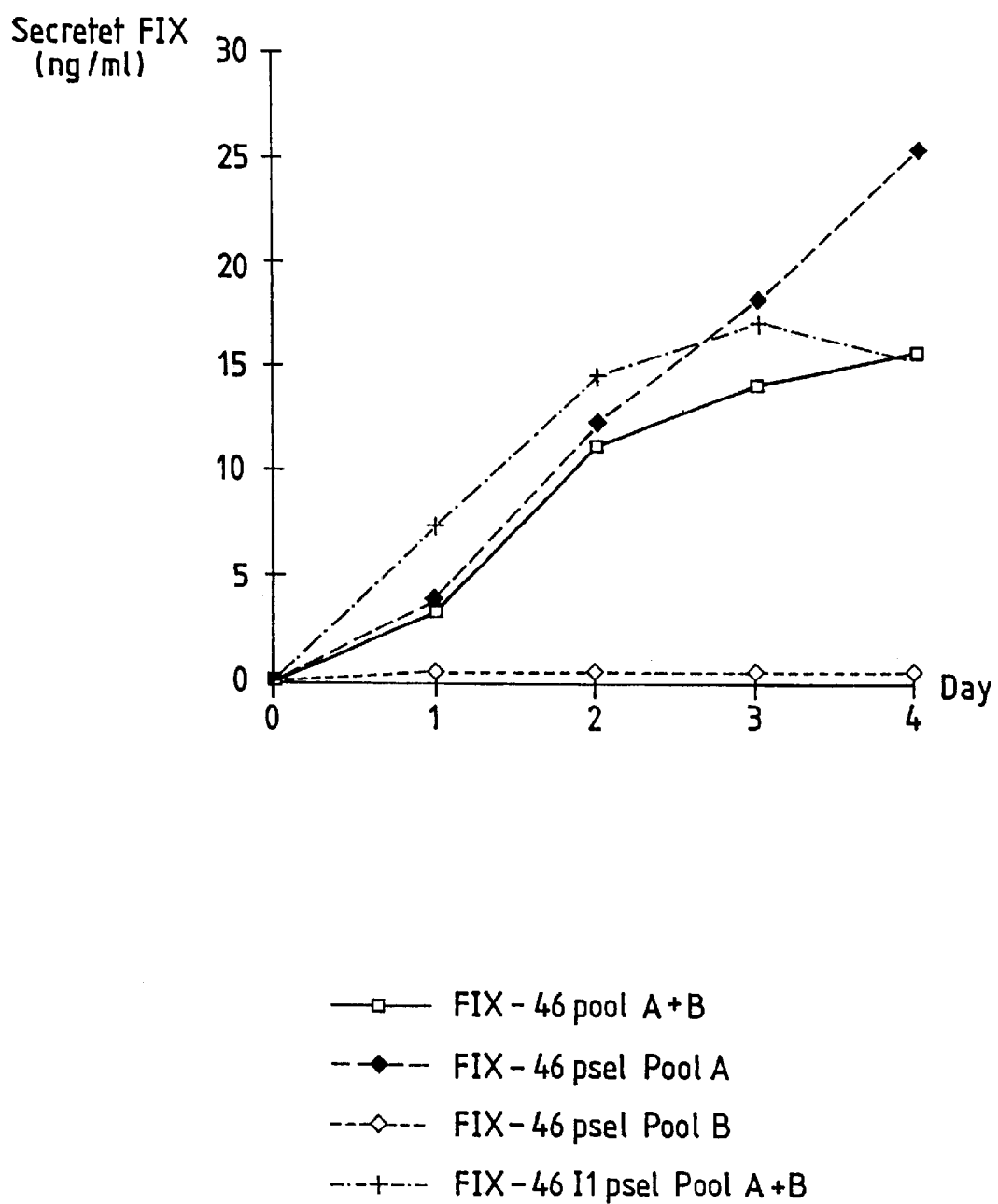
Figure 7:
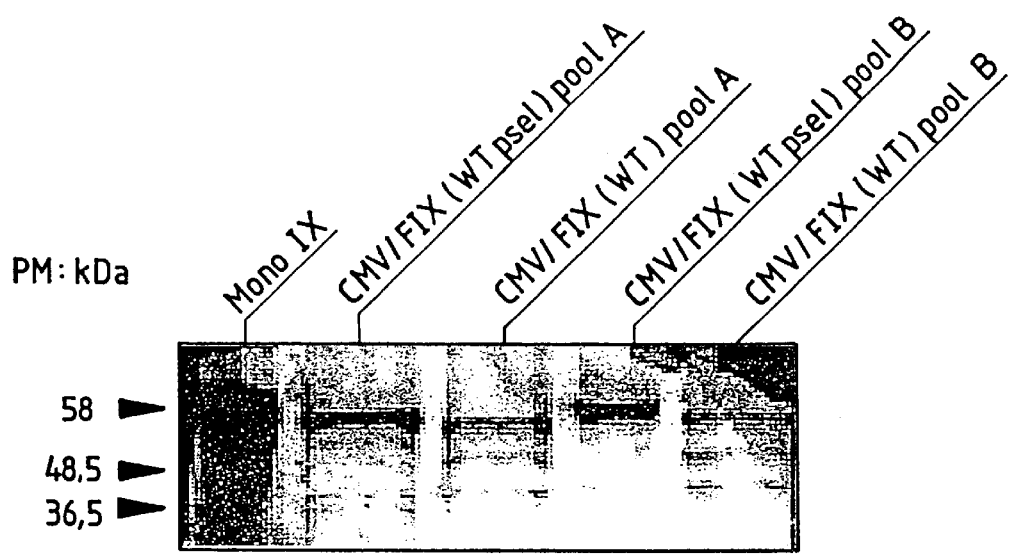
Figure 8:
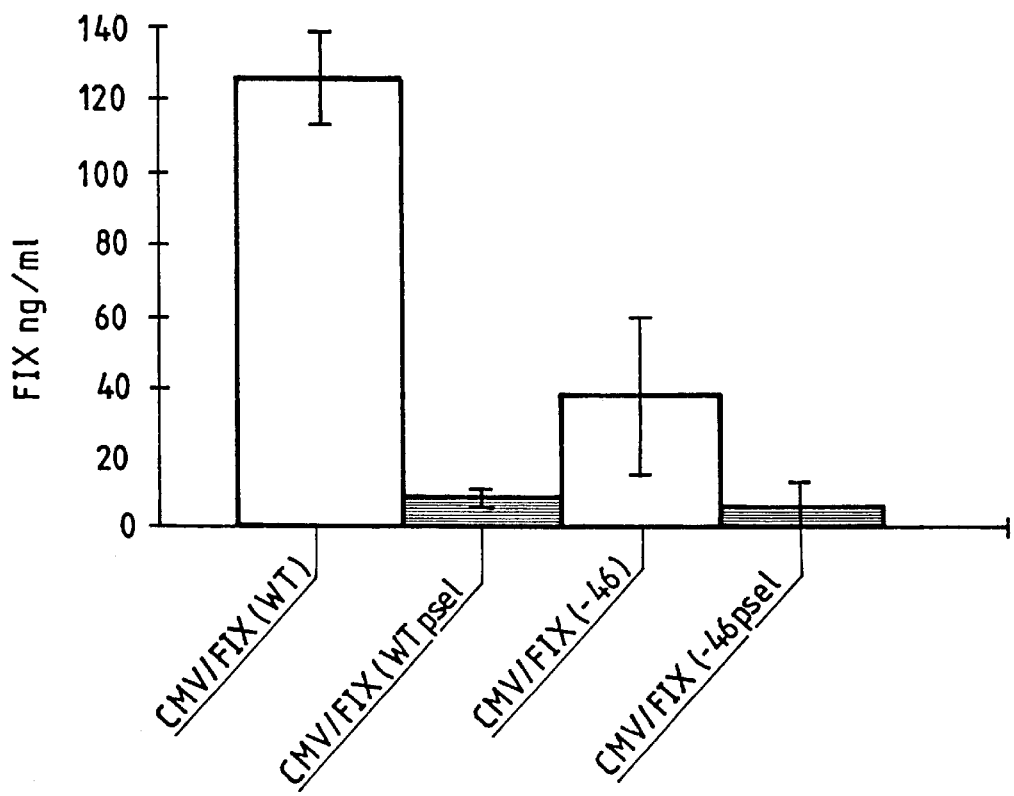
Figure 9A:
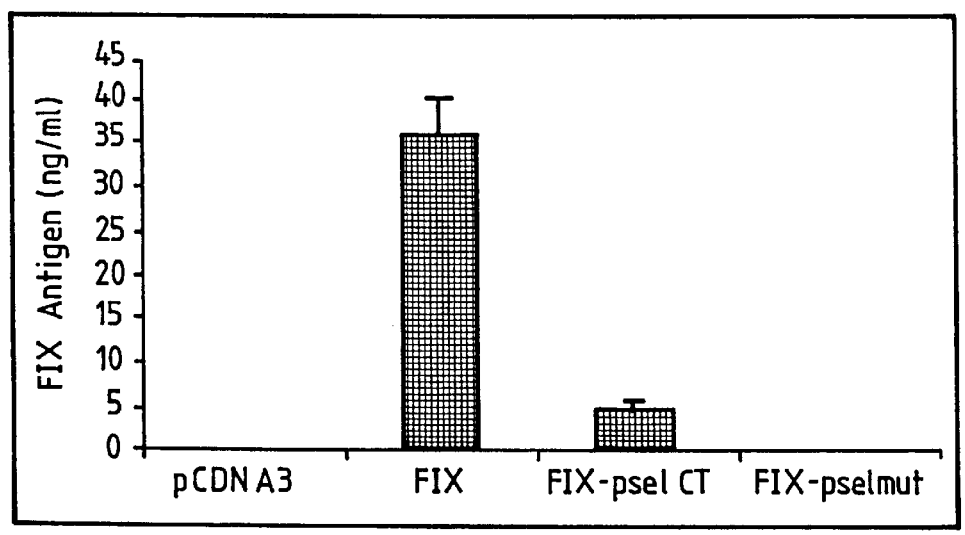
Figure 9B:
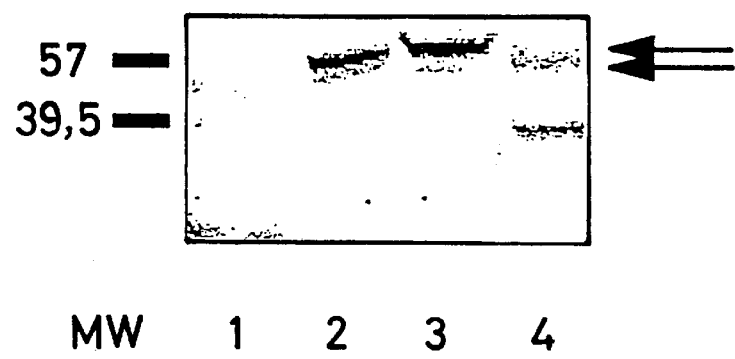
Figure 10A:
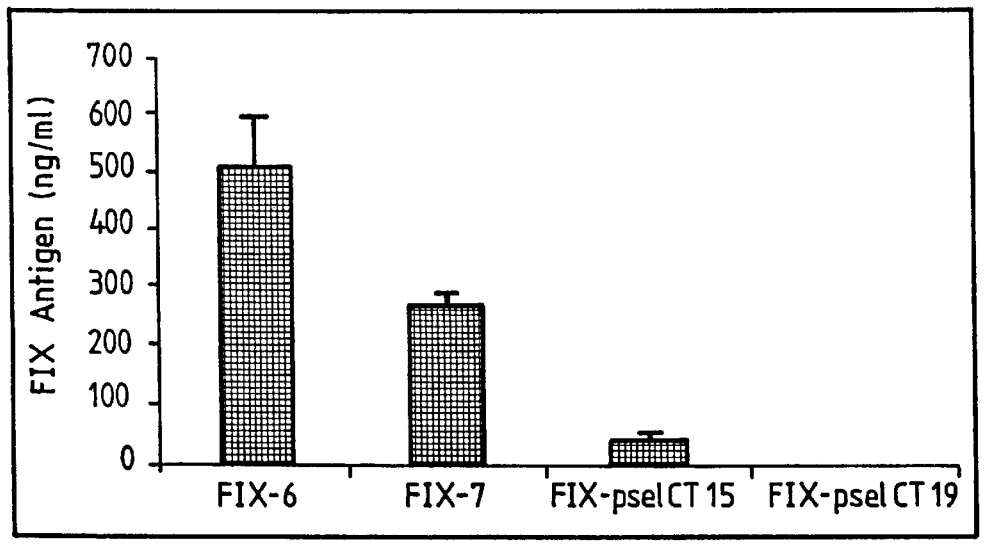
Figure 10B:
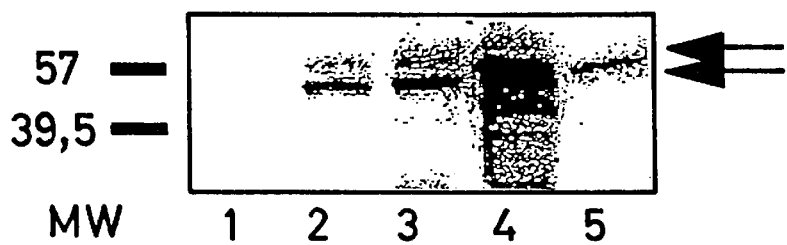
Figure 11:
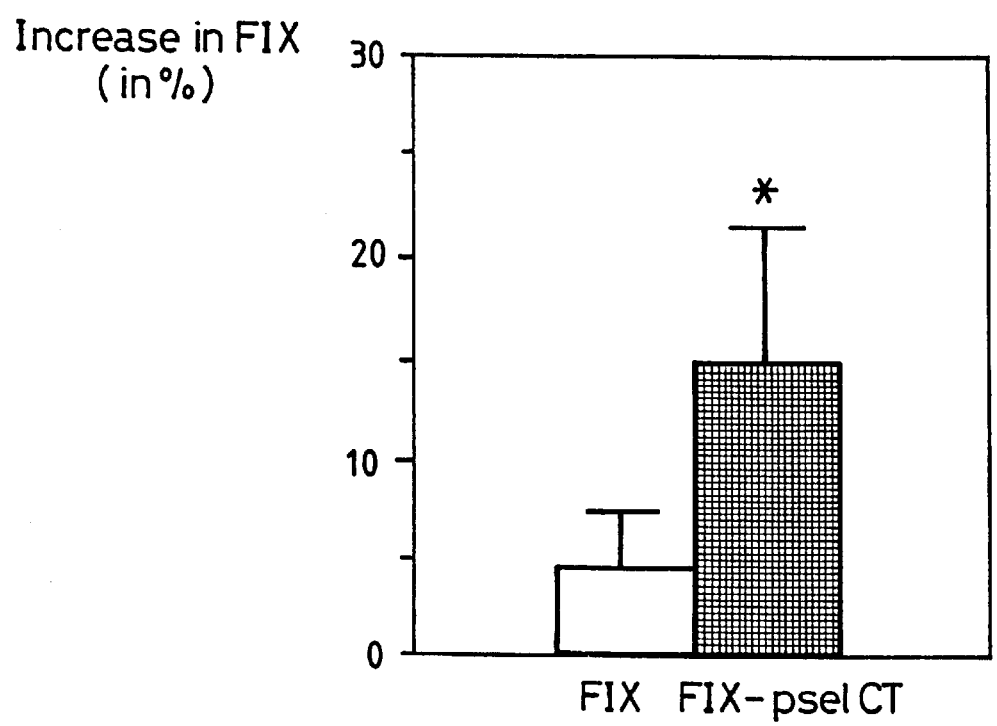

Subject of this invention are DNA constructs encoding fusion proteins comprising amino acid sequences of blood coagulation factors and of P-Selectin.

P-Selectin is an integral transmembrane glycoprotein expressed in endothelial cells and platelets. P-Selectin is an inducible molecule implicated in cell-to-cell adhesion. The molecule is stored on resting cells in particular sub-cellular compartments: Weibel-Palade bodies in endothelial cells and a-granules in platelets. The intracellular domain of P-Selectin (psel) was shown to be responsible for the targeting of the molecule in different compartments: storage granules, lysosomes, dense-core granules and synaptic-like-microvesicles [2, 4, 5]. Two chimeric molecules were generated using this domain: Tissue-Factor-psel and Horse-Radish Peroxidase (HRP)-psel. In both cases, using secretion-regulated cell lines (AtT20 and PC12), the chimeric molecules were directed into secretory granules and lysosomes [2, 6]. The intracellular tail possesses two distinct stretches of amino acids implicated in the targeting. The 10 amino acids close to the plasma membrane direct P-Selectin and HRP-psel in lysosomes, whereas the 3'extremity is required for the targeting in synaptic-like microvesicles, i.e., secretory vesicles [1, 6]. The targeting potential of the cytoplasmic tail was also shown to be increased in the presence of the transmembrane domain. When both domains were present, a chimeric E-selectin-P-selectin was more efficiently directed into granules [3].

The addition of the P-Selectin tail seems to represent an interesting tool for targeting genetic factors of therapeutic interest into intracellular storage compartments where they can be useful for somatic gene therapy. The present invention shows that DNA constructs of blood clotting factors like Factor IX and of P-Selectin create new possibilities for the treatment of patients suffering from a defiency of blood coagulation factors. It is directed to chimeric molecules comprising inter alia FIX-DNA constructs fused with the cytoplasmic domain of P-Selectin.

It has been found that a DNA construct encoding a fusion protein comprising an amino acid sequence of a blood clotting factor and an amino acid sequence of the cytoplasmic domain of human P-Selectin retains the full blood coagulation activity and has valuable properties which are useful for the somatic gene therapy of patients suffering from a defiency of a blood coagulation factor like Factor IX.

The invention is illustrated by the attached FIG. I to XIII.

FIG. I shows the pcDNA3-FIX(-46) construct and the pcDNA3-FIX WT construct;

FIG. II shows the first intron (Intron I) of the human FIX gene as truncated by using two sides Sca I;

FIG. III shows the pcDNA-FIX(-46.I1) and the pcDNA-FIX (WT.I1) construct;

FIG. IV shows the pcDNA3-FIX(-46)psel and the pcDNA-FIX (WT)psel construct;

FIG. V shows the pcDNA3-FIX(-46-I1)psel and the pcDNA-FIX (WT-I.1)psel construct;

FIG. VI shows the secretion of FIX in pools of different constructs;

FIG. VII shows the immunoblotting of FIX in CHO-lysates;

FIG. VIII shows the psel sequence effect on the amount of FIX secreted by CHO-cells;

FIG. IX$a$ shows the expression levels of the FIX, FIX-psel and FIX-pselmut proteins in CHO cells;

FIG. Ix$b$ shows the immunoblotting of the cell lysates of FIX-psel and FIX-pselmut;

FIG. X$a$ shows the expression levels of FIX and FIX-psel in AtT20 cell line;

FIG. X$b$ shows the immunoblotting of the cell lysates of FIX and FIX-psel in AtT20 cell line;

FIG. XI shows the increase in FIX and FIX-psel release after 8-Br-cAMP stimulation.

A—Construction of the Chimeric Molecules

1. Generation of the FIX cDNAs

Total RNAs were prepared using Promega™mRNA extraction kit from human liver. Factor FIX(46)cDNA was obtained by RT-PCR using Reverse Transcriptase (Promega™, France) and Taq polymerase (Appligene-Oncor™, France). Two FIX primers were used: 5'FIX(-46) creating a NcoI site at 5' (with a Kozak modification [7]) and 3' FIX Stop creating a XhoI site in the 3' end of the cDNA FIX(-46) (see Table I). The FIX cDNA was cloned in an initial intermediate vector named pUT535 (Cayla, Toulouse, France). FIX(-46) was sequenced and shown to present a single point mutation CGC→CCC (in the sequence corresponding to the signal peptide: Pro-44Arg). However, since pcDNA3.1 vector (Invitrogen, the Netherlands) is bearing more restriction enzyme sites and neomycine resistance gene this vector appeared to be more convenient for the next studies. FIX(-46) cDNA was digested by PstI and XhoI, cloned in pBlueScript (Stratagene™) and then inserted in the expression vector pcDNA3 after a BamHI and XhoI digestion to obtain pcDNA3-FIX(-46) (FIG. I).

To obtain the FIX wildtype, a new primer was designed: 5'FIXWT containing the 3 ATG in frame without any Kozak modification and correcting the Pro-44Arg mutation. The 3' primer was 3'FIX AvaI located on the AvaI site of the FIX cDNA (see Table I). A 679 bp PCR product was obtained and cloned in PCR 2.1 vector (In Vitrogen) and sequenced. A 484 bp fragment of the PCR product was directly cloned in pcDNA3-FIX(-46) by partial BamHI-EcoRV digestion to obtain pcDNA3-FIX WT (FIG. I).

2. Generation of the FIX.I1 cDNAs

During the attempts to improve FIX constructs, the presence of intron I was shown to dramatically increase the ability of cells to produce FIX. The efficient expression of many mammalian genes depends on the presence of at least one intron. The first intron (Intron I) of the human FIX gene has been previously suggested to have an expression-increasing activity [8]. Therefore, this first intron being truncated by using two sites Sca I, as shown in FIG. II, was cloned into FIX-46 cDNA. The construct was prepared as follows:

The 5'part of the FIX Intron I was amplified by PCR from genomic DNA between the 5' end of ATG -46 of exon I (5' FIX-46 primer) and a PvuII site at 5' end of the Intron I (5' FIX Intron I primer) (see Table I). A second fragment was amplified between 3' end of the Intron I (3' FIX Intron I primer) and the 5' end of the exon II (3' FIX Exon II primer) (see Table I). The two PCR fragments were then ligated in PvuII site and further digested with ScaI to obtain a 300 bp fragment. The 300 bp fragment was sequenced and shown to be free of mutations. This 300 bp Intron I was further cloned in the constructs pcDNA3-FIX(-46) and pcDNA3-FIX(WT) using EcoRV digestion to obtain pcDNA3-FIX(-46.I1) and pcDNA3-FIX(WT.I1) (FIG. III).

3. Generation of a 3' End-modified FIX and Generation of the Hybrid Psel cDNAs

In order to fuse the 3' end of the FIX to the psel fragment, a 700 bp PCR fragment was obtained by amplifying FIX(-46) cDNA between the AvaI site (FIX 5' AvaI primer) and the stop codon (see Table I). The 3' antisense oligonucleotide (FIX 3' MluI primer) contained a MluI site replacing the stop codon by an arginine codon (see Table I).

A 111 bp sequence corresponding to the 35 amino acids located at the 3'-end of the human P-Selectin was amplified by RT-PCR from human platelet mRNA (primers: 5' GMP MIuI and 3' GMP XhoI) (see Table I).

psel amino acid sequence: RKRFRQKDDGKCPLNPHS-HLGTYGVFTNAAFDPSP (=SEQ ID No.1)

This sequence was fused after the 3'-end-modified FIX(-46) sequence by the MIuI site. This fusion required the addition of two amino acids (Thr-Arg) between FIX and psel. A WhoI site was added at the 3'-end after the stop codon for further cloning.

In order to introduce the 111 bp psel in all the other FIX constructs, a 3'-end modified FIX/psel fragment digested by BstBI was obtained from pcDNA3-FIX(-46.psel) and further introduced in the different FIX vectors opened by the same enzyme (see FIG. IV). Using this strategy, pcDNA3-FIX(-46.I1.psel), pcDNA3-FIX.WT-psel and pcDNA3-FIX.WT.I1.psel were obtained (see FIG. V).

Aminoacids Sequences of FIX C-terminus Part, P-Selectin 5'Part of the Intracellullar Domain and the Fused Protein The 3'end of the P-Selectin transmembrane domain is indicated in bold.

| FIX 3' end | THR LYS LEU THR STOP |
|---|---|
| P-SEL 5' Tail | ALA LEU LEU ARG LYS ARG |
| FIX-psel | THR LYS LEU THR THR ARG ARG LYS ARG |

4-Generation of a Control FIX Molecule Containing a Random Peptidic Fragment

A random sequence issued from human factor VIII cDNA with a frame-shift was amplified by PCR using the Expand System (Roche Molecular Diagnostics, Meylan, France). This 106 bp length sequence was generated by the oligonucleotides 12C (5'-AAC GCG TAT TCT TTT ACA TTT CAG GTC TAT GGA TTC TGG GGT GCC ACA AC)(=SEQ.ID.No.13) and pselmut 3' (5'-ACT CGA GTC ACA ACT TGA AAC CTT C)(=SEQ.ID.No.14) The resulting amino-acid sequence added at the FIX carboxy terminus was TRILLHPRSMDSGVPNLRLSENRHDRLTESPKI (SEQ.ID. No.15) and did not show any homology with described proteins identified so far in the NCBI database. The PCR fragment bears the Mlu I site in its 5'-end and an Xho I site in its 3'-end. The fragment was cloned at the 3' end of pcDNA3-FIX WT-psel after removal of the psel fragment.

B—Characterization of the Chimeric Molecules

1.Stable Expression of FIX Psel in CHO Cells

All constructs were transfected into CHO cells (purchased from ECACC) by electroporation. $6 \times 10^6$ cells were transfected with 10 mg of Sca I or Pvu I (when Intron I was present) linearized DNA. Sixteen hours after transfection the medium was removed and replaced with fresh medium containing 0.6 mg/ml G418. This concentration was previously shown to be the lowest efficient concentration on non-transfected CHO cells. Seven days after transfection G418 resistant clones were visible. Two strategies were therefore conducted. The first one consisted of picking up 10 individual colonies for expansion. In the second strategy, the colonies present in an entire 90 mm dish were pooled corresponding approximately to 20 to 100 clones. This pool was then expanded and two pools (A and B) were done for each construct. Clones and cellular pools were then frozen. Cell culture supernatants were collected and stored at −80° C.

FIG. VII shows the immunoblotting of FIX in CHO CMV/FIX WT+/−psel lysates. Lysates from exponentially growing cells were subjected to electrophoresis on SDS-PAGE/10% polyacrylamide gel and semi-dry blotted onto nitrocellulose membrane. FIX was identified with a polyclonal rabbit anti-human FIX antibody (Dako, Trappes, France). The protein was detected using the ECL System (Amersham).

FIG. VIII shows the psel sequence effect on FIX amounts secreted by CHO CMV/FIX WT or CMV/FIS-46+/−psel. FIX accumulation was measured for the two pools in duplicate by independent experimenters after 3 days of culture. FIX antigen was quantified in the supernatant using an ELISA kit (Asserachrom IX: Ag, Stago, Asnièsres, France).

2. The Kinetic of Psel Production

The ability of FIX-46-psel to be secreted was followed with a kinetic study of FIX production that was compared to FIX46. FIX-46-psel and FIX-46 II-psel were both used. 35 mm Petri dishes were seeded with $4 \times 10^5$ cells and 2 ml of vitamin supplemented medium. The conditioned mediums were collected after 1 to 4 days of conditioning. For each supernatant, the FIX antigen accumulation was assessed with ELISA (Asserachrom VIIIC.AG, Diagnostica Stago, Asnières, France). The kinetic of FIX-psel gave quite homogeneous results. In contrast, the two FIX46-psel pools gave totally different results: pool B showing no FIX-psel secretion whereas pool A showing a level of production similar to the other constructs. Because of this important discrepancy their respective protein production was not combined. All constructs (except for pool B) roughly gave a similar FIX antigen production in supernatants (see FIG. VI).

3. FIX-Psel is Able to Induce Blood Coagulation

The procoagulant activity was measured in the supernatants from CHO, FIX-46, FIX-46-psel and FIX-46 II-psel transfected cells using the one-stage clotting assay with Factor IX-depleted plasma. The activity was roughly similar in all FIX containing supernatants. However, since the measurements were done on unpurified material (containing 10% FCS, other CHO secretion and degradation products) no definite conclusions could be drawn concerning the value of the different production levels. The main point was to check the procoagulant property of FIX-psel protein.

| Cellular type | Fix-46 | Fix-46 P-sel | Fix-46 I1P-sel |
|---|---|---|---|
| Activity (mU/ng antigen) | 4.4+/−3.2 | 4.4+/2.5 | 3.2+/−0.8 |

Table II: Specific activity of different FIX molecules

These values represent the average of at least three measurements on all pools A.

4. FIX-Psel Present in Higher Amounts in CHO Cells

Immunoblotting

A sample of all cell lines were lysed and an equal amount of total cell lysates (60 mg) was submitted to immunoblotting using anti-FIX antibodies from DA(Rabbit) Anti-Human Factor IX ref. A0300). CHO cells expressing FIX-46 showed barely detectable protein whereas all constructs coding for chimeric proteins gave high intracellular FIX levels. Here again the FIX-46-psel pool B gave the lowest, but detectable, protein production, being consistant with the kinetic of production.

In the two pools of FIX-46 I1-psel, the anti-FIX antibody revealed two bands. An immunoprecipitation done on the cell supernatant showed that these two compounds are both secreted.

Immunoprecipitation

The same amount of Triton-soluble lysates (850 mg) from different transfected cells was subjected to immunoprecipitation and revealed by the same antibody as in immunoblotting experiments. As expected, control CHO cells did not express FIX. FIX-46 from transfected cells was revealed after immunoprecipitation but in lesser extent than FIX-46-psel, being consistent with direct immunoblotting results. In addition, a slight shift in migration of FIX-46-psel was detected due to an increase in the molecular weight coming from the addition of psel.

FAC Scan Analysis

The intracellular amount of FIX-psel was then compared to control by FACS analysis. Cells were trypsinized, washed, fixed in 0.5% paraformaldehyde (PFA) and permeabilized by 0.5% Tween-20 during incubation with the first antibody. When the secondary antibody alone was used, no labelled cells in each population were detected. When the two antibodies were used (Rabbit anti-human FIX followed by an FITC-coupled anti rabbit) on non-permeabilized cells a little shift in fluorescence was observed in cells expressing the chimeric protein. This weak signal may be due to a partial permeabilization of the cells by PFA. When the cells were permeabilized, a unique major peak of fluorescence was observed in FIX transfected cells. In cells transfected with chimeras a main peak possessing a mean fluorescence intensity similar to the control peak was observed plus a shoulder corresponding to a mixed population of more intensely labelled cells. These results confirm the data obtained in immunoblotting experiments suggesting that the cells expressing the chimeric molecule retain a part of the FIX psel production.

Immunofluorescence

FIX antigen was detected by immunofluorescence. This experiment is done on cellular pools. Therefore the percentage of labelled cells varied from 40 to 60% from pools to pools and different levels of expression were present in a single population. Among the labelled cells, some differences in signal intensities were observed between the different transfected cell lines. In FIX-46 expressing cells a very faint signal was observed but clearly higher than the one from non-permeabilized cells. In FIX-46-psel and FIX-46 Il-psel some cells exhibit a clear signal compared either to non-permeabilized cells or to FIX-46 expressing cells. The fluor-escence was detected as punctuate all over the cytoplasm. This pattern was also found in some FIX-46 cells but in a less bright extent. This indicates that psel does not seem to be able to generate per se in CHO cells a distinct structure such as Weibel-Palade bodies.

5. The P-selectin Intracellular Domain Specifically Retains FIX-WT in CHO Cells All cDNA constructs (pcDNA3, FIX WT, FIX-psel and FIX-pselmut) were stably transfected in CHO cells. The amounts of secreted Factor IX are presented in FIG. IXa. As expected no FIX antigen was found in supernatant from CHO cells transfected with the vector alone. The maximum FIX production was obtained with cells expressing wild-type FIX (36.1 ng/ml+/−4.2, mean+/−SD). Factor IX-psel expression level was decreased 7.7 times in the supernatants (4.7ng/ml+/−1.1) as compared to the factor amounts with FIX WT without P-sel fragment. A chimera between FIX and a random sequence (FIX-pselmut) was barely detectable (0.4 ng/ml+/−0.03).

To evaluate whether the reduced secretion of FIX-psel and FIX-pselmut was the result of an impairment of the factor IX biosynthesis, an immunoblot was done on cell lysates (FIG. IXb). In contrast with the data from the cell supernatant, a larger amount of FIX-psel was found in the cell lysates compared to FIX. FIX and FIX-psel patterns of migration were similar with a slight shift in the migration of FIX-psel. This shift was reproducibly observed and was due to the addition of the psel fragment. In contrast, the FIX-pselmut was almost not detectable in cell lysates. These results clearly indicate that the FIX-psel is retained in CHO cells through the specific properties of the P-Selectin tail.

6- FIX WT-psel is Specifically Directed in the Storage Granules of AtT20 Cells The mouse anterior pituitary derived cell line (AtT20) was a gift from Dr. J. P.Rosa (INSERM U 348, Paris). They were maintained at 37° C. under 10% $CO_2$ in DME medium, pH 7.8 (Gibco BRL Life Technologies) supplemented with 10% fetal calf serum and 1 ng/ml vitamin K. AtT20 cells ($3.5 \times 10^6$) were transfected by Fugene 6 (Roche Molecular Diagnostics) with 2 mg DNA of pcDNA3-FIX, pcDNA3-FIX-psel or pcDNA3-FIX-11-psel vectors linearized by Pvu I. Six hours after transfection the medium was removed and replaced by fresh medium. Geneticin at 0.6 mg/ml was added 16 hours later. Thirty clones of each construct were picked and screened for FIX expression by measuring FIX antigen in the supernatant. Further detailed analyses were conducted on the 2 to 4 best FIX-producing clones.

As in CHO cells a dramatic difference in the amount of FIX produced was detected between two FIX and two FIX-psel expressing clones (510+/−93 and 277+/−9.6 ng/ml vs. 39+/−5.8 and 2.23+/−0.07 ng/ml, mean +/−SD) (FIG. Xa). An immunoblot analysis was conducted on cell lysates. The two FIX expressing clones exhibited a similar amount of intracellular FIX, whereas the protein amount produced by the FIX-psel clones was heterogeneous (FIG. Xb). In one case (FIG. Xb lane 4) the amount of FIX-psel retained in the cells was higher than the FIX control (FIG. XB lanes 2 and 3). In the other case (FIG. Xb lane 5) the quantity of FIX-psel detected in the cell lysate was slightly lower than the control. However, the ratio of FIX antigen stored vs. FIX secreted showed that in both clones the FIX-Psel was preferentially retained in the cells since the intracellular/extracellular ratios were at least 15 times larger for FIXpsel than for FIX (Table II)

Table II. Ratio of intracellular FIX antigen versus secreted FIX antigen.

|   | Secreted Fix (ng/ml) | Intracellular amount (Relative Unit) | Ratio (In/Out) |
| --- | --- | --- | --- |
| FIX-6 | 510+/−93 | 70 | 0.14 |
| FIX-7 | 277+/−9.6 | 93 | 0.33 |
| FIX-pselCT 15 | 39+/−5.8 | 188 | 5 |
| FIX-pselCT 19 | 2.23+/007 | 62 | 25 |

$2 \times 10^5$ cells were seeded in a 35 mm Petri dish. The supernatants were collected 3 days after when cells were exponentially growing. Secreted FIX antigen concentration were determined by ELISA. The result presented is representative of two independent experiments (n=3 for each). To determine the FIX intracellular amounts, cells were lysed and an immunoblot was performed. The FIX signal was integrated using the NIH Image 1.61 software. The data presented are representative of immunoblots produced with 2 independent cell lysates (n=2 for each).

When wild-type FIX and FIX-psel transfected AtT 20 cells were examined for FIX immunoelectron microscopy, the following results were observed: Wild type FIX did not exhibit consistent labeling for FIX in any recognizable structures. Occasional gold particles were scattered in the cytoplasmic background but did not precisely label definite structures (data not shown). In contrast FIX-psel AtT20 transfected cells displayed FIX labeling within cisternae of the Golgi complex associated vesicles and in condensing vacuoles which are the precursor structures of secretion granules (Disdier, et al., 1992). Electron dense granules also displayed gold labeling within their matrix and this labeling co-localized with ACTH immunolabeling confirming that these structures were secretion granules (data not shown).

Since the extracellular production of FIX by FIX-psel transfected clones was generally weak, we used pcDNA3-FIX I1-psel construct to improve the protein production. The addition of the FIX truncated intron 1 in the FIX cDNA was indeed shown to induce a roughly 10 times higher FIX production in HepG2 and CHO cells ((8) and (9)). When the psel tail was added at the 3' end of such a construct, the resulting protein was secreted in larger quantities compared to pcDNA3-FIX-psel, but it was also preferentially stored to the same extent as found when FlXpsel was used.

To evaluate whether FIX and FIX-psel could be secreted from the AtT20 storage granules, eight different clones (4 FIX, 2 FIX-psel and 2 FIX 11-psel) were stimulated by the 8-Br-cAMP (5). All clones were first checked to be responsive to the secretion by measuring the release of ACTH. After the addition of 8-Br-cAMP, a mean increase of 67% +/−23; mean +/−SD (range 41 to 100%) in secreted ACTH compared to non-treated cells was observed. Following this stimulation, FIX and FIX-psel antigen both increased in the supernatants. However, the average FIX-psel increase was significantly higher than FIX (14.9%+/−6.9 vs. 4.43%+/−2.9; mean +/−SD) indicating that FIX-psel could be effectively secreted following 8-Br-cAMP stimulation (FIG. XI)

In conclusion, the CHO- and AtT20-transfected cells secrete FIX protein without storage but when the P-selectin cytoplasmic tail is fused with the FIX, the chimeric molecule is both stored and secreted. The storage of the FIX-psel is specifically due to the psel tail since a random fragment did not allow the production of a functional FIX molecule. The FIX-psel possesses a procoagulant activity comparable to the wild-type and exhibits a a slight molecular weight increase due to the P-Selectin tail. In the At120 cell line the FIX-psel is specifically directed to the endogenous storage granules and could be released from these granules after cellular stimulation. The addition of the P-Selectin tail is therefore an interesting tool for targeting FIX or other molecules in intracellular storage compartments. This is the first time that a soluble molecule (devoid of transmembrane domain) is targeted by the P-Selectin intracellular domain. Furthermore the activity of the molecule is retained.

BIBLIOGRAPHY (1) Blagoveshchenskaya, A. D., Norcott, i. P. & Cutler, D. F. (1998). Lysosomal targeting of P-selectin is mediated by a novel sequence within its cytoplasmic tail. J. Biol. Chem. 273, 2729–2737
(2) Disdier, M., Morrissey, J. H., Fugate, R. D., Bainton, D. F. & McEver, R. P. (1992). Cytoplasmic domain of P-selectin (CD62) contains the signal for sorting into the regulated secretory pathway. Mol. Biol. Cell. 3, 309–21
(3) Fleming, J. C., Berger, G., Guichard, J., Cramer, E. M. & Wagner, D. D. (1998). The transmembrane domain enhances granular targeting of P-selectin. Eur. i. Cell. Biol. 75, 331343
(4) Green, S. A., Setiadi, H., McEver, R. P. & Kelly, R. B. (1994). The cytoplasmic domain of P-selectin contains a sorting determinant that mediates rapid degradation in lysosomes. J.Cell. Biol. 124, 434–48
(5) Koedam, J. A., Cramer, E. M., Briend, E., Furie, B. C. & Wagner, D. D. (1992). P-selectin, a granule membrane protein of platelets and endothelial cells, follows the regulated secretory pathway in AtT-20 cells. J. Cell. Biol. 116, 617–25
(6) Norcott, J. P., Solari, R. & Cutler, D. F. (1996). Targeting of P-selectin to two regulated secretory organelles in PC12 cells. J. Cell. Biol. 134,1229–1240
(7) Kozak, M. (1986). Point Mutations define a sequence flanking the AUG initiator codon that modulares translation by eukariotic ribosomes. Cell 44, 283–292
(8) Kurachi, S., Hitomi, Y., Furukawa, M. & Kurachi, K. (1995). Role of Intron 1 in the expression of the human factor IX gene. J. Biol. Chem. 270, 5276–5281.
(9) Enjolras N., Rodriguez M-H., Plantier J-L., Maurice M., Attali O. and Nègrier C, The three in frame ATG of FIX are required for an optimal protein production. Thromb Haemost 1999 (in press).

TABLE I

Primer Sequences for FIX Constructs
(for details see the attached Sequence Listing)

| Primers | Sequences (5' → 3') | SEQ ID |
|---|---|---|
| 5'FIX(-46) | ACACCCATGGAGCGCGTGAACATGATCATGG | No. 2 |
| 5'FIX WT | TGGATCCATGCAGCGCGTGAACATGATCATGG | No. 3 |
| 3'FIX atop | AAAACTCGAGTTAAGTGAGCTTTGTTTTTTCC | No. 4 |
| 3'FIX Mlu I | AAAAACGCGTAGTGAGCTTTGTTTTTTCCTTAA | No. 5 |
| 3'FIX Ava I | AACAACCCGAGTGAAGTC | No. 6 |
| 5'FIX Ava I | AATGACTTCACTCGGGTTGTTGG | No. 7 |
| 5'GMP Mlu I | AAAAACGCGTAGAAAGCGTTTCAGACAAAAAG | No. 8 |
| 3'GMP Xho I | AAAACTCGAGTTAAGGACTCGGGTCAAATGC | No. 9 |
| 5'FIX Intron I | ATTTCACAGCTGACATCATGTCTGG | No. 10 |
| 3'FIX Intron I | ACCAGCTGCAATGAAAATAAGGG | No. 11 |
| 3'FTX Exon II | ATTTTGTTGGCGTTTTCATGATCAAG | No. 12 |

What is claimed is:

1. A DNA construct encoding a fusion protein comprising an amino acid sequence of a blood clotting factor and an amino acid sequence of the cytoplasmic domain of P-Selectin.

2. The DNA construct as claimed in claim 1 comprising an amino acid sequence of the blood clotting factor IX.

3. The DNA construct as claimed in claim 2 wherein the 3'-end of the Factor IX-DNA is fused to the 5' end of the nucleic acid sequence encoding the cytoplasmic domain of intracellular P-selectin.

4. The DNA construct as claimed in claim 2 wherein between the sequence of the Factor IX-DNA and the sequence of the P-Selectin-DNA the two amino acids Thr-Arg are inserted.

5. The DNA construct as claimed in claim 2 further comprising insertion of the first intron (Intron 1) of the human Factor IX gene.

6. The DNA construct as claimed in claim 5 wherein the first intron has been truncated at both Sca 1 sites prior to insertion.

7. A fusion protein expressed by the DNA construct of claim 1.

8. A mammalian cell comprising the DNA construct of claim 1, wherein the DNA construct is expressed.

9. The mammalian cell wherein the DNA construct of claim 1 encodes Factor IX.

* * * * *

UNITED STATES PATENT AND TRADEMARK OFFICE
CERTIFICATE OF CORRECTION

PATENT NO.     : 6,419,921 B1                                        Page 1 of 1
DATED          : July 16, 2002
INVENTOR(S)    : Claude Négrier et al.

It is certified that error appears in the above-identified patent and that said Letters Patent is hereby corrected as shown below:

Column 14,
Line 23, "cell" should read -- cell of claim 8 --.
Lines 23 and 24, delete "of claim 1".

Signed and Sealed this

Eleventh Day of March, 2003

JAMES E. ROGAN
*Director of the United States Patent and Trademark Office*